United States Patent [19]

Eidenschink et al.

[11] Patent Number: 4,600,528
[45] Date of Patent: Jul. 15, 1986

[54] DECALIN-CARBONITRILES

[75] Inventors: Rudolf Eidenschink, Dieburg; Georg Weber, Erzhausen, both of Fed. Rep. of Germany

[73] Assignee: Merck Patent Gesellschaft mit Beschränkter Haftung, Darmstadt, Fed. Rep. of Germany

[21] Appl. No.: 616,441

[22] Filed: Jun. 1, 1984

[30] Foreign Application Priority Data

Jun. 1, 1983 [DE] Fed. Rep. of Germany ....... 3319781

[51] Int. Cl.$^4$ ............... C09K 3/34; G02F 1/13; C07D 319/06; C07C 121/46; C07C 121/00
[52] U.S. Cl. ............... 252/299.61; 252/299.5; 252/299.62; 252/299.63; 350/350 R; 544/294; 549/372; 549/373; 549/374; 549/375; 558/423; 558/414; 558/411; 558/419
[58] Field of Search ............... 252/299.61, 299.62, 252/299.63, 299.5; 350/350 R; 549/372, 373, 373, 375; 544/294; 260/464, 465 D, 465 C, 465 F, 465 G, 465 H

[56] References Cited

U.S. PATENT DOCUMENTS

| | | | |
|---|---|---|---|
| 4,386,007 | 5/1983 | Krause et al. | 252/299.62 |
| 4,406,814 | 9/1983 | Ferrato | 252/299.62 |
| 4,421,670 | 12/1983 | Deutscher et al. | 252/299.62 |
| 4,432,885 | 2/1984 | Petrzilka et al. | 252/299.62 |
| 4,434,073 | 2/1984 | Sucrow et al. | 252/299.62 |
| 4,438,268 | 3/1984 | Zaschke et al. | 252/299.61 |
| 4,510,069 | 4/1985 | Eidenschink et al. | 252/299.61 |

FOREIGN PATENT DOCUMENTS

| | | | |
|---|---|---|---|
| 210920 | 6/1984 | German Democratic Rep. | 252/299.62 |
| 2082179 | 3/1982 | United Kingdom | 252/299.62 |

*Primary Examiner*—Teddy S. Gron
*Attorney, Agent, or Firm*—Millen & White

[57] ABSTRACT

New decalin-carbonitriles of the formula I

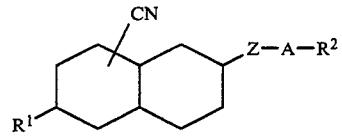

wherein $R^1$ is an alkyl group with 1–10 C atoms, it being possible for up to two $CH_2$ groups to be replaced by O atoms, Z is $-CH_2CH_2-$, $-CO-O-$, $-O-CO-$, $-O-CH_2-$, $-CH_2O-$ or a single bond, A is 1,4-phenylene, 1,4-cyclohexylene, 1,3-dioxane-2,5-diyl, 1,4-bicyclo(2,2,2)octylene, pyrimidine-2,5-diyl or a single bond, and $R^2$ is an alkyl group with 1 to 10 C atoms, it being possible for up to two $CH_2$ groups to be replaced by O atoms, or is F, Cl, Br, CN, $-O-COR^3$ or $-COOR^3$, or, if at least one of the groups Z and A is not a single bond, can also be H and $R^3$ is alkyl of 1 to 6 C atoms, and the acid addition salts of basic compounds of this type, are suitable for use as components of liquid crystal dielectrics.

12 Claims, No Drawings

DECALIN-CARBONITRILES

BACKGROUND OF THE INVENTION

Certain decalin compounds having two substituents are known from British Pat. No. 2,082,179.

SUMMARY OF THE INVENTION

It is an object of the present invention to provide new decalin-based compounds having valuable properties, e.g., as liquid crystalline substances, e.g. to provide new stable liquid crystal or mesogenic compounds which are suitable as components of liquid crystal di-electrics.

These objects have been achieved by providing new decalin-carbonitriles of the formula I

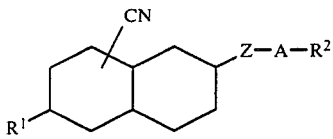    I wherein $R^1$ is an alkyl group with 1–10 C atoms, it being possible for up to two non-adjacent $CH_2$ groups to be replaced by 0 atoms, Z is $-CH_2CH_2-$, $-CO-O-$, $-O-CO-$, $-O-CH_2-$, $-CH_2O-$ or a single bond, A is 1,4-phenylene, 1,4-cyclohexylene, 1,3-dioxane-2,5-diyl, 1,4-bicyclo(2,2,2)-octylene, pyrimidine-2,5-diyl or a single bond, and $R^2$ is an alkyl group with 1 to 10 C atoms, it being possible for up to two non-adjacent $CH_2$ groups to be replaced by 0 atoms, or is F, Cl, Br, CN, $-O-COR^3$ or $-COOR^3$, or, if at least one of the groups Z and A is not a single bond, can also be H and $R^3$ is alkyl of 1 to 6 C atoms, and the acid addition salts of basic compounds of this type.

DETAILED DISCUSSION

For simplicity, in the following text "Phe" is a 1,4-phenylene group, "Cy" is a 1,4-cyclohexylene group, "Dio" is a 1,3-dioxane-2,5-diyl group, "Bi" is a bicyclo-(2,2,2)-octylene group, "Pyr" is a pyrimidine-2,5-diyl group and "Dec" is the group

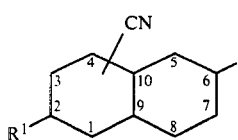

Compounds of the formula I can be used as components of liquid crystal dielectrics in the same way as similar compounds, in particular for displays based on the principle of the twisted cell, the guest-host effect, the effect of deformation of orientation phases and the effect of dynamic scatter.

It has been found that the compounds of the formula I are outstandingly suitable as components of liquid crystal dielectrics. In particular, stable liquid crystal phases having a highly negative dielectric anisotropy and hence a small threshold or control voltage of electrooptical effects, very little optical anisotropy and comparatively low viscosity can be prepared with the aid of these compounds.

In addition, with the provision of the compounds of the formula I, the range of liquid crystal substances suitable, from various technological viewpoints, for the preparation of nematic mixtures is quite generally substantially widened.

The compounds of the formula I have a broad field of application. Depending on the choice of substituents, these compounds can be used as basic materials from which liquid crystal dielectrics are predominatly composed; however, compounds of the formula I can also be added to basic liquid crystal materials from other classes of compounds, for example in order to reduce the dielectric and/or optical anisotropy of such a dielectric. The compounds of the formula I are furthermore suitable as intermediates for the preparation of other substances which can be used as constituents of liquid crystal dielectrics.

The compounds of the formula I are colorless in the pure state and form liquid crystal mesophases in a temperature range which is favorably placed for electrooptical use. They are very stable towards chemicals, heat and light.

The invention thus relates to the compounds of the formula I and to a process for their preparation, characterized in that a compound which otherwise corresponds to the formula I but contains one or more reducible groups and/or C—C bonds instead of H atoms is treated with a reducing agent, or in that HCN is added onto a compound which otherwise corresponds to the formula I but contains no CN group in the decalin radical but an additional double bond, or in that, for the preparation of esters of the formula I (wherein Z is $-CO-O-$ or $-O-CO-$, or wherein $R^2$ is $-O-COR^3$ or $-COOR^3$), a corresponding carboxylic acid or one of its reactive derivatives is reacted with a corresponding alcohol or one of its reactive derivatives, or in that, for the preparation of dioxane derivatives of the formula I (where A is 1,3-dioxane-2,5-diyl), a corresponding aldehyde is reacted with a corresponding diol, or in that a corresponding carboxylic acid amide is dehydrated or a corresponding carboxylic acid halide is reacted with sulfamide or a corresponding chlorine or bromine compound is reacted with a cyanide, or in that, for the preparation of decalin-2- or -6-carbonitriles of the formula I, a nitrile of the formula II

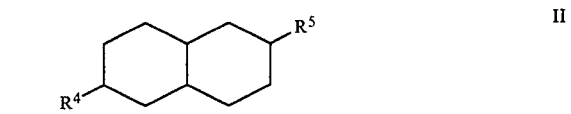    II wherein (a) $R^4$ is CN and $R^5$ is $-Z-A-R^2$, or (b) $R^4$ is $R^1$ and $R^5$ is CN, and $R^1$, A, Z and $R^2$ have the meanings given, is reacted with a compound of the formula III

Q—X    III wherein Q is (a) $R^1$ or (b) $R^2-A-Z-$ and X is Cl, Br, I, OH or a reactive esterified OH group, and $R^1$, A, Z and $R^2$ have the meanings given, or in that a compound which corresponds to the formula I but, instead of a C—C bond between the C atom carrying the CN group and a C atom adjacent to this, contains an additional H atom (on the C atom carrying the CN group) and an additional group X (on the C atom adjacent to this, X having the meaning given), is cyclized, HX being split off, or in that, for the preparation of ethers of the formula I (wherein $R^1$ and/or $R^2$ are alkyl chains, up to 2 $CH_2$ groups being replaced by 0 atoms, and/or Z is a —OCH₂— or —CH₂O— group), a corresponding hydroxy compound is etherified, and/or in that, if appropriate, a base of the formula I is converted into one of its acid addition salts by treatment with an acid, or in that, if appropriate, a compound of the formula I is liberated from one of its acid addition salts by treatment with a base.

The invention furthermore relates to the use of compounds of the formula I as components of liquid crystal dielectrics. The invention moreover relates to liquid crystal dielectrics containing at least one compound of the formula I and electrooptical display elements containing such dielectrics.

A, Q, $R^1$, $R^2$, $R^3$, $R^4$, $R^5$, X and Z above and below have the meaning given, unless expressly indicated otherwise.

The compounds of the formula I accordingly include compounds of the part-formulae Ia to Ijj:

| | |
|---|---|
| Dec—CH₂CH₂—Phe—R² | Ia |
| Dec—CH₂CH₂—Cy—R² | Ib |
| Dec—CH₂CH₂—Dio—R² | Ic |
| Dec—CH₂CH₂—Bi—R² | Id |
| Dec—CH₂CH₂—Pyr—R² | Ie |
| Dec—CH₂CH₂—R² | If |
| Dec—CO—O—Phe—R² | Ig |
| Dec—CO—O—Cy—R² | Ih |
| Dec—CO—O—Dio—R² | Ii |
| Dec—CO—O—Bi—R² | Ij |
| Dec—CO—O—Pyr—R² | Ik |
| Dec—CO—O—R² | Il |
| Dec—CO—O—CO—Phe—R² | Im |
| Dec—O—CO—Cy—R² | In |
| Dec—O—CO—Dio—R² | Io |
| Dec—O—CO—Bi—R² | Ip |
| Dec—O—CO—Pyr—R² | Iq |
| Dec—O—CO—R² | Ir |
| Dec—O—CH₂—Phe—R² | Is |
| Dec—O—CH₂—Cy—R² | It |
| Dec—O—CH₂—Dio—R² | Iu |
| Dec—O—CH₂—Bi—R² | Iv |
| Dec—O—CH₂—Pyr—R² | Iw |
| Dec—O—CH₂—R² | Ix |
| Dec—CH₂—O—Phe—R² | Iy |
| Dec—CH₂—O—Cy—R² | Iz |
| Dec—CH₂—O—Dio—R² | Iaa |
| Dec—CH₂—O—Bi—R² | Ibb |
| Dec—CH₂—O—Pyr—R² | Icc |
| Dec—CH₂—O—R² | Idd |
| Dec—Phe—R² | Iee |
| Dec—Cy—R² | Iff |
| Dec—Dio—R² | Igg |
| Dec—Bi—R² | Ihh |
| Dec—Pyr—R² | Iii |
| Dec—R² | Ijj |

(In Ijj, $R^2$ is not H). Z is preferably a single bond. A is preferably a single bond or Cy. Compounds of the formulae Iff and Ijj are accordingly preferred.

The CN group in the decalin system is preferably on one of the tertiary C atoms, in particular in the 2- or 9-position; however, it can also be in the 6- or 10-position, and furthermore in the 1-, 3-, 4-, 5-, 7- or 8-position.

In the compounds of the formulae above and below, $R^1$ and $R^2$ are preferably alkyl, and furthermore alkoxy (especially if these radicals are on a Phe group) or another oxaalkyl group.

X is preferably Cl or Br, but also I, OH or reactively esterified OH, such as alkylsulfonyloxy with, in particular, 1–6 C atoms (for example methylsulfonyloxy) or arylsulfonyloxy with, in particular, 6–10 C atoms (for example phenyl-, p-tolyl- or naphthyl-sulfonyloxy).

In the compounds of the formulae above and below, the alkyl radicals, in which one ("alkoxy" or "oxaalkyl") or two ("alkoxyalkoxy" or "dioxaalkyl") CH₂ groups can also be replaced by 0 atoms, can be straight-chain or branched. Preferably, they are straight-chain, have 2, 3, 4, 5, 6 or 7 C atoms and accordingly are preferably ethyl, propyl, butyl, pentyl, hexyl, heptyl, ethoxy, propoxy, butoxy, pentoxy, hexoxy, heptoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl and 2-, 3-, 4-, 5- or 6-oxaheptyl, and furthermore methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl and 1,3-, 1,4-, 1,5-, 1,6-, 2,4-, 2,5-, 2,6-, 3,5-, 3,6- or 4,6-dioxaheptyl.

Compounds of the formulae I and Ia to Ijj with branched wing groups $R^1$ and/or $R^2$ can occasionally be of importance because of their better solubility in the usual basic liquid crystal materials, but in particular as chiral doping substances, if they are optically active. Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 2-methylheptoxy, 3-oxa-3-methylbutyl and 3-oxa-4-methylpentyl.

Of the compounds of the formulae I and Ia to Iz those in which at least one of the radicals contained therein has one of the given preferred meanings and/or wherein the CN group is in one of the given preferred positions are preferred. Particularly preferred smaller groups of compounds are those of the formulae Ikk and Ill:

Dec—alkyl                                  Ikk

Dec—Cy—alkyl                         Ill

Those stereoisomers of trans-decalin in which the groups $R^1$ and —Z—A—$R^2$ are equatorial and the CN group is axial are preferred here.

Those of the abovementioned formulae which contain one of the groups Dio or Pyr include in each case the two possible 2,5- and 1,4-position isomers. Thus, for example, the part formula Igg includes 2-Dec-5-$R^2$-1,3-dioxanes and 2-$R^2$-5-Dec-1,3-dioxanes, and the part formula Iii includes the 2-Dec-5-$R^2$-pyrimidines and the 2-$R^2$-5-Dec-pyrimidines.

The compounds of the formula I can be prepared by methods which are known per se, such as are described in the literature (for example in the standard works, such as Houben-Weyl, Methoden der Organischen Chemie (Methods of Organic Chemistry), Georg-Thieme Verlag, Stuttgart), and in particular under reaction conditions which are known and suitable for the reactions mentioned. Variants which are known per se and are not mentioned in more detail here can also be utilized.

If desired, the starting substances can also be formed in situ, such that they are not isolated from the reaction mixture but are immediately reacted further to give the compounds of the formula I.

Thus, the compounds of the formula I can be prepared by reducing a compound which otherwise corresponds to the formula I but contains one or more reducible groups and/or C—C bonds instead of H atoms.

Preferred suitable reducible groups are carbonyl groups, in particular keto groups, and furthermore, for example, free or esterified hydroxyl groups or aromatically bonded halogen atoms. Preferred starting substances for the reduction correspond to the formula I, but can contain a naphthalene, di-, tetra-, hexa- or octahydronaphthalene or di-, tetra-, hexa-, octa- or decahydronaphthalenone ring instead of the decalin ring, or a cyclohexene ring or cyclohexanone ring instead of a cyclohexane ring, and/or a —CH=CH— group or a —CH$_2$CO— group instead of a —CH$_2$CH$_2$— group.

The reduction is carried out under conditions under which the CN group remains intact, preferably by catalytic hydrogenation at temperatures between about 0° and about 100° and under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Preferred suitable catalysts are noble metals, such as Pt or Pd, which can be used in the form of oxides (for example PtO$_2$ or PdO), on a support (for example Pd-on-charcoal, -calcium carbonate or -strontium carbonate) or in finely divided form.

Compounds of the formula I can furthermore be obtained by adding hydrogen cyanide onto a corresponding octahydronaphthalene derivative (which otherwise corresponds to the formula I, but contains no CN group in the decalin radical but instead an additional double bond).

This addition reaction is carried out, for example, in the presence of an inert solvent, for example a halogenated hydrocarbon, such as $CH_2Cl_2$ or $CHCl_3$, a nitrile, such as acetonitrile, or an amide, such as dimethylformamide (DMF), at temperatures between about −10° and +150° and under pressures between about 1 and 100 bar. It may be advantageous to add catalysts, for example adding on of HCN can be catalyzed by addition of palladium bis-[2,3-O-isopropylidene-2,3-dihydroxy-1,4-bis-(diphenylphosphino)butane].

Esters of the formula I (Z=—CO—O— or —O—CO—, or $R^2$=—O—COR$^3$ or —COOR$^3$, that is to say those of the part formulae Dec—CO—O—A—$R^2$, Dec—O—CO—A—$R^2$, Dec—Z—A—O—CO—$R^3$ or Dec—Z—A—COOR$^3$) can also be obtained by esterification of corresponding carboxylic acids of the formulae Dec—COOH, $R^2$—A—COOH, $R^3$—COOH or Dec—Z—A—COOH (or their reactive derivatives with alcohols or phenols of the formulae $R^2$—A—OH, Dec—OH, Dec—A—OH or $R^3$—OH (or their reactive derivatives).

Particularly suitable reactive derivatives of the carboxylic acids mentioned are the acid halides, in particular the chlorides and bromides, and furthermore the anhydrides, for example also mixed anhydrides of the formulae Dec—CO—O—CO—CH$_3$, $R^2$—A—CO—O—CH$_3$, $R^3$—CO—O—CO—CH$_3$ and Dec—Z—A—CO—O—CO—CH$_3$, azides or esters, in particular alkyl esters with 1-4 C atoms in the alkyl group.

Particularly suitable reactive derivatives of the alcohols and phenols mentioned are the corresponding metal alcoholates and phenolates of the formulae $R^2$—A—OM, Dec—OM, Dec—Z—A—OM and $R^3$—OM, wherein M is one equivalent of a metal, preferably an alkali metal, such as Na or K.

The esterification is advantageously carried out in the presence of an inert solvent. Ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane, are particularly suitable. Water-immiscible solvents can at the same time advantageously be used for removal by azeotropic distillation of the water formed during the esterification. An excess of an organic base, for example pyridine, quinoline or triethylamine, can also occasionally be used as the solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are as a rule ended after 15 minutes to 48 hours.

Specifically, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, important bases being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonates, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or phenol into the sodium or potassium alcoholate or phenolate, for example by treatment with ethanolic sodium hydroxide solution or potassium hydroxide solution, isolating this alcoholate or phenolate, suspending it in acetone or diethyl ether, together with sodium bicarbonate or potassium carbonate, with stirring, and adding a solution of the acid chloride or anhydride in diethyl ether, acetone or DMF to this suspension, preferably at temperatures between about $-25°$ and $+20°$.

Dioxane derivatives of the formula I (wherein the group A is a 1,3-dioxane-2,5-diyl group) are preferably prepared by reacting a corresponding aldehyde of the formula Dec—Z—CHO or $R^2$—CHO (or one of its reactive derivatives) with a corresponding 1,3-diol of the formula $R^2$—CH(CH$_2$OH)$_2$ or Dec—Z—CH(CH$_2$OH)$_2$ (or one of its reactive derivatives), preferably in the presence of an inert solvent, such as benzene or toluene, and/or a catalyst, for example a strong acid, such as sulfuric acid or benzene- or p-toluene-sulfonic acid, at temperatures between about 20° and about 150°, preferably between 80° and 120°. Suitable reactive derivatives of the starting substances are, in particular, acetals, for example of the formulae Dec—Z—CH(OR$^6$)$_2$, $R^2$—CH(OR$^6$)$_2$, $R^2$—CH(CH$_2$O)$_2$—CHR$^7$ and Dec—Z—CH(CH$_2$O)$_2$—CHR$^7$, wherein $R^6$ is alkyl with 1-4 C atoms and two radicals $R^6$ together can also be alkylene with 2 or 3 C atoms, and $R^7$ is H, alkyl with 1-4 C atoms or phenyl.

Some of the aldehydes and 1,3-diols mentioned and their reactive derivatives are known, and some of them can be prepared without difficulty from compounds which are known from the literature by standard methods of organic chemistry. For example, the aldehydes can be obtained by oxidation of corresponding alcohols or by reduction of corresponding carboxylic acids or their derivatives, and the diols can be obtained by reduction of corresponding diesters.

To prepare the nitriles of the formula I, corresponding acid amides which contain a CONH$_2$ group instead of the CN group can be dehydrated. The amides can be obtained, for example, from the corresponding esters or acid halides by reaction with ammonia. Examples of suitable dehydrating agents are inorganic acid chlorides, such as SOCl$_2$, PCl$_3$, PCl$_5$, POCl$_3$, SO$_2$Cl$_2$ and COCl$_2$, and furthermore P$_2$O$_5$, AlCl$_3$ (for example as a double compound with NaCl) and aromatic sulfonic acids and sulfonic acid halides. The reaction here can be carried out in the presence or absence of an inert solvent at temperatures between about 0° and 150°; examples of suitable solvents are bases, such as pyridine or triethylamine, aromatic hydrocarbons, such as benzene, toluene or xylene, and amides, such as DMF.

To prepare the nitriles of the formula I, it is also possible to react corresponding acid halides, preferably the chlorides, with sulfamide, preferably in an inert solvent, such as tetramethylene sulfone, at temperatures between about 80° and 150°, preferably at 120° After customary working up, the nitriles can be isolated directly.

To prepare the nitriles of the formula I, it is also possible to react a corresponding chlorine or bromine compound with a cyanide, preferably with a metal cyanide, such as NaCN, KCN or Cu$_2$(CN)$_2$, for example in the presence of pyridine in an inert solvent, such as DMF or N-methylpyrrolidone, at temperatures between 20° and 200°.

The preferred nitriles of the formula I, wherein the nitrile group is in the 2- or 6-position, can preferably also be obtained by reacting nitriles of the formula II with compounds of the formula III. The nitriles of the formula II can be obtained, for example, from corresponding halides (corresponding to formula II, but Cl or Br instead of CN) and metal cyanides, and the compounds of the formula III—where these are not known—can be obtained by reduction of corresponding carboxylic acid esters to the corresponding hydroxy compounds (III, X=OH) and, if appropriate, reaction thereof with inorganic halides, such as SOCl$_2$, HBr or HI; preferred compounds of the formula III are those in which Q is alkyl, $R^2$—C$_y$— or $R^2$—A—CH$_2$—CH$_2$—. The nitrile II is preferably first converted into the corresponding carbanion with a strong base, such as NaH, NaNH$_2$, lithium diisopropylamide, piperidide or 2,5-diisopropylpiperidide or K tert.-butylate, preferably in an inert solvent, for example a hydrocarbon, such as toluene, an ether, such as THF or dioxane, an amide, such as DMF, a sulfoxide, such as dimethylsulfoxide or a mixture of such solvents. After addition of III (wherein X is other than OH), the mixture is preferably kept at temperatures between −30° and 100° for 0.5 to 16 hours. In contrast, reaction of II with III (X=OH) is preferably effected in the presence of azodicarboxylic acid esters/triphenylphosphine in THF at temperatures between about −30° and +30°.

In a completely analogous manner, nitriles of the formula I can be obtained by "intramolecular alkylation", by cyclizing a nitrile which corresponds to the formula I but, instead of a C—C bond between the C atom carrying the CN group and a C atom adjacent to this, contains an additional H atom (on the C atom carrying the CN group) and an additional group X (on the C atom adjacent to this), HX being split off.

Examples of suitable starting substances for this "intramolecular alkylation" are compounds of the formulae IVa to IVt:

for 1—cyano—2—R$^1$—6—(Z—A—R$^2$)—decalins:

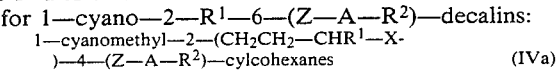

(IVa)

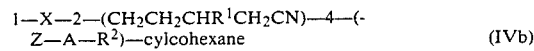

(IVb)

for 2—cyano—2—R$^1$—6—(Z—A—R$^2$)—decalins:

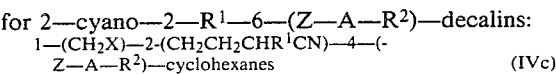

(IVc)

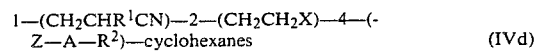

(IVd)

for 3—cyano—2—R$^1$—6—(Z—A—R$^2$)—decalins:

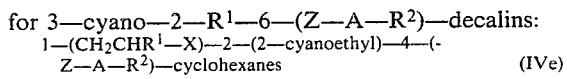

(IVe)

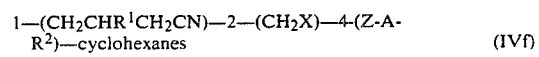

(IVf)

for 4—cyano—2—R$^1$—6—(Z—A—R$^2$)—decalins:

1—(CH₂CHR¹CH₂CH₂CN)—2—X—4—(-Z—A—R²)—cyclohexanes (IVg)

1—(CH₂CHR¹CH₂X)—2—cyanomethyl—4—(-Z—A—R²)—cyclohexanes (IVh)

for 5—cyano—2—² —6—(Z—A—R²)—decalins:
1—cyanomethyl—2—(CH₂CH₂—CHX-—Z—A—R²)—4—R¹—cyclohexanes (IVi)

1—X—2—[CH₂CH₂—CH(Z—A—R²)—CH₂CN]—4—R¹—cyclohexanes (IVj)

for 6—cyano—2—R¹—6—(Z—A—R²)—decalins:
1—(CH₂X)—2—[CH₂CH₂—CH(CN)—Z—A—R²]—4—R¹—cyclohexanes (IVk)

1—[CH₂—CH(CN)—Z—A—R²]—2—(CH₂CH₂X)—4—R¹—cyclohexanes (IVl)

for 7—cyano—2—R¹—6—(Z—A—R²)—decalins:
1—(CH₂—CHX—Z—A—R²)—2—(2—cyanoethyl)—4—R¹—cyclohexanes (IVm)

1—[CH₂—CH(Z—A—R²)—CH₂CN]—2—(CH₂X)—4—R¹—cyclohexanes (IVn)

for 8—cyano—2—R¹—6—(Z—A—R²)—decalins:
1—[CH₂CH(Z—A—R²)—CH₂CH₂CN]—2—X—4—R¹—cyclohexanes (IVo)

1—[CH₂CH(Z—A—R²)—CH₂X]—2—cyanomethyl—4—R¹—cyclohexanes (IVp)

for 9—cyano—2—R¹—6—(Z—A—R²)—decalins:
1—[CH₂—CH(Z—A—R²)—CH₂CH₂X]—2—cyano—4—R¹—cyclohexanes (IVq)

1—cyano—2—(CH₂CH₂—CHR¹—CH₂X)—4—(-Z—A—R²)—cyclohexanes (IVr)

for 10—cyano—2—R¹—6—(Z—A—R²)—decalins:
1—cyano—2—[CH₂CH₂—CH(Z—A—R²)—CH₂X]—4—R¹—cyclohexanes (IVs)

1—(CH₂—CHR¹—CH₂CH₂X)—2—cyano—4—(-Z—A—R²)—cylcohexanes (IVt)

The starting substances of the formulae IVa to IVt can be prepared, for example, from the corresponding carboxylic acids via the corresponding chlorides and amides.

Ethers of the formula 1 (wherein R¹ and/or R² are alkyl chains in which up to two CH₂ groups are replaced by 0 atoms and/or in which Z is a —OCH₂— or —CH₂O— group) can be obtained by etherification of corresponding hydroxy compounds, preferably corresponding phenols, the hydroxy compound preferably first being converted into a corresponding metal derivative, for example into the corresponding alkali metal alcoholate or alkali metal phenolate by treatment with NaOH, KOH, Na₂CO₃ or K₂CO₃. This metal derivative can then be reacted with the corresponding alkyl halide or sulfonate or dialkyl sulfate, preferably in an inert solvent, such as acetone, DMF or dimethylsulfoxide, or in an excess of aqueous or aqueous-alcoholic NaOH or KOH at temperatures between about 20° and 100°.

A base of the formula I can be converted into the associated acid addition salt with an acid. Acids which can be used for this reaction are inorganic acids, for example sulfuric acid, nitric acid, hydrogen halide acids, such as hydrochloric acid or hydrobromic acid, phosphoric acids, such as orthophosphoric acid, and sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -di-sulfonic acids and lauryl-sulfuric acid.

Conversely, it is possible to liberate the base of the formula I from an acid addition salt of a compound of the formula I by treatment with a base, for example with a strong inorganic base, such as KOH or NaOH.

The dielectrics according to the invention comprize 2 to 15, preferably 3 to 12, components, at least one of which is a compound of the formula I. The other constituents are preferably selected from the nematic or nematogenic substances, in particular the known substances, from the classes of azoxybenzenes, benzylidineanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-dioxanes, optionally halogenated stilbenes, benzyl phenyl ethers, tolanes and substituted cinnamic acids.

The most important compounds which are suitable as constituents of such liquid crystal dielectrics can be characterized by the formula V

R—L—G—E—R'  V wherein L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

—CH=CH—

—CH=CY—

—C≡C—

—CO—O—

—CO—S—

—CH=N—

—N(O)=N—

—CH=N(O)—

—CH₂—CH₂—

—CH₂—O—

—CH₂—S—

—COO—Phe—COO— or a C—C single bond, Y is halogen, preferably chlorine, or —CN and R and R' are alkyl, alkoxy, alkanoyloxy or alkoxycarbonyloxy with up to 18, preferably up to 8, carbon atoms, and one of these radicals can also be CN, NC, $NO_2$, $CF_3$, F, Cl or Br.

In most of these compounds, R and R' are different from one another, one of these radicals usually being an alkyl or alkoxy group. However, other variants of the envisaged substituents can also be used. Many such substituents or mixtures thereof are commercially available.

The dielectrics according to the invention contain about 0.1 to 100%, preferably 10 to 100%, of one or more compounds of the formula I.

The dielectrics according to the invention are prepared in a manner which is customary per se. As a rule, the components are dissolved in one another, preferably at elevated temperature.

The liquid crystal dielectrics according to the invention can be modified by suitable additives such that they can be used in all the types of liquid crystal display elements which have as yet been disclosed.

Such additives are known to the expert and are described in detail in the literature. For example, conductive salts, preferably ethyl-dimethyl-dodecyl-ammonium 4-hexyloxybenzoate, tetrabutylammonium tetraphenylboronate or complex salts of crown ethers (compare, for example, i. Haller et al., Mol. Cryst. Liq. Cryst., Volume 24, pages 249–258 (1973) can be added to improve the conductivity, dichroic dyestuffs can be added to prepare color guest-host systems or substances can be added for modification of the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728, and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

"Customary working up" means: water is added, the mixture is extracted with methylene chloride, the organic phase is separated off, dried and evaporated and the produce is purified by crystallization and/or chromatography.

EXAMPLE 1

A solution of 35.3 g of 2-propyl-6-cyano-6-(p-methoxybenzoylmethyl)-trans-decalin (obtainable from anisole and 2-propyl-6-cyano-6-trans-decalyl-acetyl chloride in the presence of $AlCl_3$) in 500 ml of THF is hydrogenated on 5 g of 10% strength Pd/C at 40° and under 1 bar until 0.2 mole of $H_2$ has been taken up. The mixture is filtered and the filtrate is evaporated to give 2-propyl-6-cyano-6-(2-p-methoxyphenylethyl)-trans-decalin.

2-Cyano-2-pentyl-6-(p-ethylphenoxymethyl)-trans-decalin is obtained analogously from 2-cyano-2-pentyl-6-(p-acetyl-phenoxymethyl)-trans-decalin.

EXAMPLE 2

28.2 g of 2-pentyl-6β-phenyl-3,4,4aα,5,6,7,8,8aβ-octahydronaphthalene (obtainable by reaction of 6β-phenyl-1H-(4aα,8aβ)-octahydronaphthalen-2-one with pentyl-MgBr, hydrolysis to 2-pentyl-6β-phenyl-3,4,4aα,5,6,7,8,8aβ-octahydronaphthalen-2-ol and dehydration), 2.7 g of liquid HCN, 0.1 g of palladium bis-[2,3-0-isopropylidene-2,3-dihydroxy-1,4-bis-(diphenylphosphino)-butane] and 100 ml of acetonitrile are heated at 130° for 1 hour in an autoclave. After cooling, evaporating and customary working up, 2β-cyano-2α-pentyl-6β-phenyl-trans-decalin is obtained.

The following compounds can be obtained analogously by addition of HCN onto the corresponding decalins:
2β-cyano-2α-propyl-6β-(trans-4-propylcyclohexyl)-trans-decalin
2β-cyano-2α-propyl-6β-(trans-4-butylcyclohexyl)-trans-decalin
2β-cyano-2α-propyl-6β-(trans-4-pentylcyclohexyl)-trans-decalin
2β-cyano-2α-propyl-6β-(trans-4-hexylcyclohexyl)-trans-decalin
2β-cyano-2α-propyl-6β-(trans-4-heptylcyclohexyl)-trans-decalin.

EXAMPLE 3

17 g of trans-4-propylcyclohexanecarboxylic acid are boiled with 24 g of $SOCl_2$ for 1 hour, the resulting crude acid chloride is dissolved in 150 ml of toluene, and 8 ml of pyridine and 16.7 g of 2-cyano-2-propyl-trans-decalin-6-ol (obtainable by alkylation of 2-cyano-trans-decalin-6-ol) are added and the mixture is boiled for 2 hours. After cooling and customary working up, 2-cyano-2-propyl-6-trans-decalyl trans-4-propylcyclohexanecarboxylate is obtained.

The following compounds are obtained analogously from the corresponding acid chlorides by esterification:
p-fluorophenyl 2-cyano-2-propyl-trans-decalin-6-carboxylate
p-cyanophenyl 2-cyano-2-pentyl-trans-decalin-6-carboxylate
2-cyano-2-pentyl-6-trans-decalyl 2-methylpyrimidine-5-carboxylate.

EXAMPLE 4

A mixture of 1.2 g of 2-propylpropane-1,3-diol, 2.33 g of 2-cyano-2-propyl-6-formyl-trans-decalin (obtainable by addition of HCN onto 2-propyl-6-hydroxymethyl-3,4,4aα,5,6,7,8,8aβ-octahydronaphthalene to give 2- cyano-2-propyl-6-hydroxymethyl-trans-decalin and oxidation), 0.01 g of p-toluenesulfonic acid and 15 ml of toluene is boiled for 3 hours, using a water separator, cooled, washed with water and evaporated. 2-(2-Cyano-2-propyl-6-trans-decalyl)-5-propyl-1,3-dioxane is obtained.

The homologous 2-(2-cyano-2-alkyl-6-trans-decalyl)-5-alkyl-1,3-dioxanes can be obtained analogously.

EXAMPLE 5

65 g of POCl$_3$ are added dropwise to a solution of 26.5 g of 2,6-dipropyl-trans-decalin-9-carboxamide (obtainable by reaction of 6-propyl-trans-decalin-2-one with propyl-MgBr to give 2,6β-dipropyl-trans-decalin-2-ol and reaction with H$_2$SO$_4$/HCOOH to give 2,6β-dipropyl-trans-decalin-9-carboxylic acid, conversion into the acid chloride and reaction with NH$_3$) in 500 ml of DMF at 50° while stirring. After the mixture has been stirred for a further hour, it is poured onto ice and worked up in the customary manner to give 2,6-dipropyl-9-cyano-trans-decalin.

The following compounds are obtained analogously by dehydration of the corresponding amides:
2-propyl-6-butyl-9-cyano-trans-decalin
2-propyl-6-pentyl-9-cyano-trans-decalin
2-propyl-6-hexyl-9-cyano-trans-decalin
2-propyl-6-heptyl-9-cyano-trans-decalin
2-butyl-6-propyl-9-cyano-trans-decalin
2,6-dibutyl-9-cyano-trans-decalin
2-butyl-6-pentyl-9-cyano-trans-decalin
2-butyl-6-hexyl-9-cyano-trans-decalin
2-butyl-6-heptyl-9-cyano-trans-decalin
2-pentyl-6-propyl-9-cyano-trans-decalin
2-pentyl-6-butyl-9-cyano-trans-decalin
2,6-dipentyl-9-cyano-trans-decalin
2-pentyl-6-hexyl-9-cyano-trans-decalin
2-pentyl-6-heptyl-9-cyano-trans-decalin
2-hexyl-6-propyl-9-cyano-trans-decalin
2-hexyl-6-butyl-9-cyano-trans-decalin
2-hexyl-6-pentyl-9-cyano-trans-decalin
2,6-dihexyl-9-cyano-trans-decalin
2-hexyl-6-heptyl-9-cyano-trans-decalin
2-heptyl-6-propyl-9-cyano-trans-decalin
2-heptyl-6-butyl-9-cyano-trans-decalin
2-heptyl-6-pentyl-9-cyano-trans-decalin
2-heptyl-6-hexyl-9-cyano-trans-decalin
2,6-diheptyl-9-cyano-trans-decalin.

EXAMPLE 6

A solution of 36.7 g of 2-propyl-6-(trans-4-propylcyclohexyl)-trans-decalin-9-carbonyl chloride (obtainable by reaction of 6-(trans-4-propylcyclohexyl)-trans-decalin-2-one with propyl-MgBr to give 2-propyl-6-(trans-4-propylcyclohexyl)-trans-decalin-2-ol, reaction with H$_2$SO$_4$/HCOOH to give 2-propyl-6-(trans-4-propylcyclohexyl)-trans-decalin-9-carboxylic acid and reaction with SOCl$_2$) and 8 g of sulfamide in 500 ml of tetramethylene sulfone is heated at 120° for 4 hours and evaporated and the residue is worked up in the customary manner. 2-Propyl-6-(trans-4-propylcyclohexyl)-9-cyano-trans-decalin is obtained.

The following compounds are obtainable analogously from the corresponding acid chlorides:
2-propyl-6-(trans-4-butylcyclohexyl)-9-cyano-trans-decalin
2-propyl-6-(trans-4-pentylcyclohexyl)-9-cyano-trans-decalin
2-propyl-6-(trans-4-hexylcyclohexyl)-9-cyano-trans-decalin
2-propyl-6-(trans-4-heptylcyclohexyl)-9-cyano-trans-decalin
2-butyl-6-(trans-4-propylcyclohexyl)-9-cyano-trans-decalin
2-butyl-6-(trans-4-butylcyclohexyl)-9-cyano-trans-decalin
2-butyl-6-(trans-4-pentylcyclohexyl)-9-cyano-trans-decalin
2-butyl-6-(trans-4-hexylcyclohexyl)-9-cyano-trans-decalin
2-butyl-6-(trans-4-heptylcyclohexyl)-9-cyano-trans-decalin
2-pentyl-6-(trans-4-propylcyclohexyl)-9-cyano-trans-decalin
2-pentyl-6-(trans-4-butylcyclohexyl)-9-cyano-trans-decalin
2-pentyl-6-(trans-4-pentylcyclohexyl)-9-cyano-trans-decalin
2-pentyl-6-(trans-4-hexylcyclohexyl)-9-cyano-trans-decalin
2-pentyl-6-(trans-4-heptylcyclohexyl)-9-cyano-trans-decalin
2-hexyl-6-(trans-4-propylcyclohexyl)-9-cyano-trans-decalin
2-hexyl-6-(trans-4-butylcyclohexyl)-9-cyano-trans-decalin
2-hexyl-6-(trans-4-pentylcyclohexyl)-9-cyano-trans-decalin
2-hexyl-6-(trans-4-hexylcyclohexyl)-9-cyano-trans-decalin
2-hexyl-6-(trans-4-heptylcyclohexyl)-9-cyano-trans-decalin
2-heptyl-6-(trans-4-propylcyclohexyl)-9-cyano-trans-decalin
2-heptyl-6-(trans-4-butylcyclohexyl)-9-cyano-trans-decalin
2-heptyl-6-(trans-4-pentylcyclohexyl)-9-cyano-trans-decalin
2-heptyl-6-(trans-4-hexylcyclohexyl)-9-cyano-trans-decalin
2-heptyl-6-(trans-4-heptylcyclohexyl)-9-cyano-trans-decalin.

EXAMPLE 7

8 g of KCN are dissolved in a little water, and a solution of 28.5 g of 2-chloro-2-propyl-6-pentyl-trans-decalin (obtainable by reaction of 6-pentyl-trans-decalin-2-one with propyl-MgBr to give 2-hydroxy-2-propyl-6-pentyl-trans-decalin and reaction with HCl) in 200 ml of ethanol is added dropwise, with stirring. After the mixture has been boiled for 3 hours, it is evaporated and the residue is worked up in the customary manner to give 2-cyano-2-propyl-6-pentyl-trans-decalin.

The following compounds are obtained analogously from the corresponding chlorine or bromine compounds:
1-cyano-2-pentyl-6-(4-propylbicyclo(2,2,2)octylene)-trans-decalin
2-methoxymethyl-4-cyano-6-p-fluorophenyl-trans-decalin
2-octyl-5-cyano-6-p-methoxymethoxyphenyl-trans-decalin
2-(2,6-dioxaheptyl)-6-(trans-4-methoxymethylcyclohexyl)-7-cyano-trans-decalin.

EXAMPLE 8

20.5 g of 2-cyano-6β-propyl-trans-decalin (obtainable by reaction of 6β-propyl-trans-decalin-2-one with triphenylphosphine-methoxymethylene and $HClO_4$ to give 2-formyl-6β-propyl-trans-decalin, conversion into the oxime and dehydration) and 41 g of butyl bromide are dissolved in 70 ml of toluene, 4.3 g of $NaNH_2$ (50% in toluene) are added and the mixture is boiled for 5 hours. Customary working up gives 2β-cyano-2α-butyl-6β-propyl-trans-decalin.

The following compounds are obtained analogously by alkylation of the corresponding nitriles:

2β-cyano-2α-methyl-6β-propyl-trans-decalin
2β-cyano-2αmethyl-6β-butyl-trans-decalin
2β-cyano-2αmethyl-6β-pentyl-trans-decalin
2β-cyano-2α-methyl-6β-hexyl-trans-decalin
2β-cyano-2α-methyl-6β-heptyl-trans-decalin
2β-cyano-2α-ethyl-6β-propyl-trans-decalin
2β-cyano-2α-ethyl-6β-butyl-trans-decalin
2β-cyano-2α-ethyl-6β-pentyl-trans-decalin
2β-cyano-2α-ethyl-6β-hexyl-trans-decalin
2β-cyano-2α-ethyl-6β-heptyl-trans-decalin
2β-cyano-2α,6β-dipropyl-trans-decalin
2β-cyano-2α-propyl-6β-butyl-trans-decalin
2β-cyano-2α-propyl-6β-pentyl-trans-decalin
2β-cyano-2α-propyl-6β-hexyl-trans-decalin
2β-cyano-2α-propyl-6β-heptyl-trans-decalin
2β-cyano-2α,6β-dibutyl-trans-decalin
2β-cyano-2α-butyl-6β-pentyl-trans-decalin
2β-cyano-2α-butyl-6β-hexyl-trans-decalin
2β-cyano-2α-butyl-6β-heptyl-trans-decalin
2β-cyano-2α-pentyl-6β-propyl-trans-decalin
2β-cyano-2α-pentyl-6β-butyl-trans-decalin
2β-cyano-2α,6β-dipentyl-trans-decalin, m.p. 9°, c.p. −90°
2β-cyano-2α-pentyl-6β-hexyl-trans-decalin
2β-cyano-2α-pentyl-6β-heptyl-trans-decalin
2β-cyano-2α-hexyl-6β-propyl-trans-decalin
2β-cyano-2α-hexyl-6β-butyl-trans-decalin
2β-cyano-2α-hexyl-6β-pentyl-trans-decalin
2β-cyano-2α,6β-dihexyl-trans-decalin
2β-cyano-2α-hexyl-6β-heptyl-trans-decalin
2β-cyano-2α-heptyl-6β-propyl-trans-decalin
2β-cyano-2α-heptyl-6β-butyl-trans-decalin
2β-cyano-2α-heptyl-6β-pentyl-trans-decalin
2β-cyano-2α-heptyl-6β-hexyl-trans-decalin
2β-cyano-2α,6β-diheptyl-trans-decalin
2β-cyano-2α-(2-methoxyethyl)-6β-propyl-trans-decalin.

EXAMPLE 8a

In analogy to Example 8, there is obtained from 2-cyano-6β-(trans-4-propylcyclohexyl)-trans-decalin [obtainable by reaction of 4-(trans-4-propylcyclohexyl)-cyclohexanone with morpholine to the enamine, reaction with methyl vinyl ketone to 2-(3-oxobutyl)-4-(trans-4-propylcyclohexyl)cyclohexanone, cyclization with NaOH to 6-(trans-4-propylcyclohexyl)-2,3,4,4a,5,6,7,8-octahydronaphthalene-2-one, reduction with $Li/NH_3$ to 6-(trans-4-propylcyclohexyl)decalin-2-one, transformation into the 2,4,6-triisopropylbenzenesulphonyl-hydrazone and reaction with KCN] and pentyl bromide 2β-cyano-2α-pentyl-6β-(trans-4-propylcyclohexyl)-trans-decalin, m.p. 61°, c.p. 104°. Analogously, there are obtained:

2β-cyano-2α-methyl-6β-(trans-4-propylcyclohexyl)-trans-decalin
2β-cyano-2α-methyl-6β-(trans-4-butylcyclohexyl)-trans-decalin
2β-cyano-2α-methyl-6β-(trans-4-pentylcyclohexyl)-trans-decalin
2β-cyano-2α-methyl-6β-(trans-4-hexylcyclohexyl)-trans-decalin
2β-cyano-2α-methyl-6β-(trans-4-heptylcyclohexyl)-trans-decalin
2β-cyano-2α-ethyl-6β-(trans-4-propylcyclohexyl)-trans-decalin
2β-cyano-2α-ethyl-6β-(trans-4-butylcyclohexyl)-trans-decalin
2β-cyano-2α-ethyl-6β-(trans-4-pentylcyclohexyl)-trans-decalin
2β-cyano-2α-ethyl-6β-(trans-4-hexylcyclohexyl)-trans-decalin
2β-cyano-2α-ethyl-6β-(trans-4-heptylcyclohexyl)-trans-decalin
2β-cyano-2α-propyl-6β-(trans-4-propylcyclohexyl)-trans-decalin
2β-cyano-2α-propyl-6β-(trans-4-butylcyclohexyl)-trans-decalin
2β-cyano-2α-propyl-6β-(trans-4-pentylcyclohexyl)-trans-decalin
2β-cyano-2α-propyl-6β-(trans-4-hexylcyclohexyl)-trans-decalin
2β-cyano-2α-propyl-6β-(trans-4-heptylcyclohexyl)-trans-decalin
2β-cyano-2α-butyl-6β-(trans-4-propylcyclohexyl)-trans-decalin
2β-cyano-2α-butyl-6β-(trans-4-butylcyclohexyl)-trans-decalin
2β-cyano-2α-butyl-6β-(trans-4-pentylcyclohexyl)-trans-decalin
2β-cyano-2α-butyl-6β-(trans-4-hexylcyclohexyl)-trans-decalin
2β-cyano-2α-butyl-6β-(trans-4-heptylcyclohexyl)-trans-decalin
2β-cyano-2α-pentyl-6β-(trans-4-butylcyclohexyl)-trans-decalin
2β-cyano-2α-pentyl-6β-(trans-4-pentylcyclohexyl)-trans-decalin
2β-cyano-2α-pentyl-6β-(trans-4-hexylcyclohexyl)-trans-decalin
2β-cyano-2α-pentyl-6β-(trans-4-heptylcyclohexyl)-trans-decalin
2β-cyano-2α-hexyl-6β-(trans-4-propylcyclohexyl)-trans-decalin
2β-cyano-2α-hexyl-6β-(trans-4-butylcyclohexyl)-trans-decalin
2β-cyano-2α-hexyl-6β-(trans-4-pentylcyclohexyl)-trans-decalin
2β-cyano-2α-hexyl-6β-(trans-4-hexylcyclohexyl)-trans-decalin
2β-cyano-2α-hexyl-6β-(trans-4-heptylcyclohexyl)-trans-decalin
2β-cyano-2α-heptyl-6β-(trans-4-propylcyclohexyl)-trans-decalin
2β-cyano-2α-heptyl-6β-(trans-4-butylcyclohexyl)-trans-decalin
2β-cyano-2α-heptyl-6β-(trans-4-pentylcyclohexyl)-trans-decalin
2β-cyano-2α-heptyl-6β-(trans-4-hexylcyclohexyl)-trans-decalin
2β-cyano-2α-heptyl-6β-(trans-4-heptylcyclohexyl)-trans-decalin

EXAMPLE 9

6 g of NaH (50% in paraffin) are added to a solution of 41.9 g of 2-[2-(2-p-toluenesulfonyloxymethyl-5-propylcyclohexyl)-ethyl]-valeronitrile (obtainable by reaction of p-propylbenzyl 2-tetrahydropyranyl ether with 2-propylsuccinic anhydride/$AlCl_3$ to give 2-(2-tetrahydropyranyloxymethyl-5-propyl-benzoylmethyl)-valeric acid, hydrogenation to 2-[2-(2-tetrahydropyranyloxymethyl-5-propylcyclohexyl)-ethyl]-valeric acid, successive reactions with $SOCl_2$ and $NH_3$ to give 2-[2-(2-hydroxymethyl-5-propylcyclohexyl)-ethyl]-valeric acid amide, dehydration with dicyclohexylcarbodiimide to give the nitrile and tosylation) in 250 ml of dimethylsulfoxide, with stirring; during this addition, the temperature is kept below 35°. The mixture is stirred for a further 2 hours and worked up in the customary manner to give 2-cyano-2,6-dipropyl-trans-decalin.

2-Cyano-2-propyl-6-methoxy-trans-decalin is obtained analogously from 2-(2-bromoethyl-4-methoxycyclohexylmethyl)-valeronitrile (obtainable by chloromethylation of 2-(m-methoxyphenyl)-ethanol to give 2-(2-chloromethyl-5-methoxyphenyl)-ethanol, reaction with diethyl propylmalonate, hydrolysis and decarboxylation to give 2-[2-(2-hydroxyethyl)-4-methoxybenzyl]-valeric acid, hydrogenation to 2-[2-(2-hydroxyethyl)-4-methoxycyclohexylmethyl]-valeric acid, conversion into the amide, reaction with $SOBr_2$ to give 2-(2-bromoethyl-4-methoxy-cyclohexylmethyl)-valeramide and dehydration).

EXAMPLE 10

A mixture of 29.7 g of 2-cyano-2-propyl-6-p-hydroxyphenyl-trans-decalin (obtainable by reaction of 4-p-hydroxyphenylcyclohexanone with morpholine to give 1-morpholino-4-p-hydroxyphenylcyclohexane, reaction with methyl vinyl ketone and cyclization to give 6-p-hydroxyphenyl-2,3,4,4a,5,6,7,8-octahydronaphthalen-2-one, hydrogenation to 6-p-hydroxyphenyl-trans-decalin-2-one, Grignard reaction with propyl-MgBr and hydrolysis to give 6-p-hydroxyphenyl-2-propyl-decalin-2-ol, dehydration and adding on of HCN), 6.9 g of $K_2CO_3$, 25 g of hexyl iodide and 250 ml of DMF is heated at 80° for 16 hours with stirring, and is then cooled and worked up in the customary manner. 2-Cyano-2-propyl-6-p-hexyloxyphenyl-trans-decalin is obtained.

The homologous 2-cyano-2-alkyl-6-p-alkoxyphenyl-trans-decalins are obtainable analogously.

Examples of dielectrics according to the invention containing at least one compound of the formula I:

Example A

A mixture is preferred from
11% of 2β-cyano-2α-pentyl-6β-propyl-trans-decalin
24% of 2β-cyano-2α-heptyl-6β-propyl-trans-decalin
21% of 2β-cyano-2α-propyl-6β-pentyl-trans-decalin
21% of 2β-cyano-2α,6β-dipentyl-trans-decalin
13% of 2β-cyano-2α-propyl-6β-heptyl-trans-decalin and
10% of 4-(trans-4-pentylcyclohexyl)-4'-(trans-4-propylcyclohexyl)-biphenyl.

Example B 2 parts by weight of the blue dyestuff 4,8-diamino-1,5-dihydroxy-2-p-methoxyphenyl-anthraquinone are dissolved in 98 parts by weight of the mixture according to Example A.

Example C

A mixture is prepared from
9% of 2β-cyano-2α-pentyl-6β-propyl-trans-decalin
19% of 2β-cyano-2α-heptyl-6β-propyl-trans-decalin
17% of 2β-cyano-2α-propyl-6β-pentyl-trans-decalin
17% of 2β-cyano-2α,6β-dipentyl-trans-decalin
10% of 2β-cyano-2α-propyl-6β-heptyl-trans-decalin and
28% of 4-ethyl-2'-fluoro-4-(trans-4-pentylcyclohexyl)-biphenyl.

Example D 2 parts by weight of the red dyestuff 1-p-dimethylaminobenzylideneamino-4-p-cyanophenylazonaphthalene are dissolved in 98 parts by weight of the mixture according to Example C.

Example E

A mixture is prepared from
13% of 2β-cyano-2α-pentyl-6β-propyl-trans-decalin
27% of 2β-cyano-2α-heptyl-6β-propyl-trans-decalin
23% of 2β-cyano-2α-propyl-6β-pentyl-trans-decalin
23% of 2β-cyano-2α,6β-dipentyl-trans-decalin and
14% of 2β-cyano-1-propyl-6β-heptyl-trans-decalin.

Example F 1 part by weight of bis-(p-isopropylphenyl)perylene-3,9-bis-carboxylate is dissolved in 99 parts by weight of the mixture according to Example E.

Example G

A mixture is prepared from
12% of 2β-cyano-2α-pentyl-6β-propyl-trans-decalin
25% of 2β-cyano-2α-heptyl-6β-propyl-trans-decalin
22% of 2β-cyano-2α-propyl-6β-pentyl-trans-decalin
22% of 2β-cyano-2α,6β-dipentyl-trans-decalin
13% of 2β-cyano-2α-propyl-6β-heptyl-trans-decalin and
6% of trans-(4-propylcyclohexyl) trans,trans-4-propylcyclohexylcyclohexane-4'-carboxylate.

Example H

A mixture is prepared from
12% of 2β-cyano-2α-pentyl-6β-propyl-trans-decalin
24% of 2β-cyano-2α-heptyl-6β-propyl-trans-decalin
21% of 2β-cyano-2α-propyl-6β-pentyl-trans-decalin
21% of 2β-cyano-2α,6β-dipentyl-trans-decalin
13% of 2β-cyano-2α-propyl-6β-heptyl-trans-decalin and
9% of p-trans-4-butylcyclohexylphenyl trans-4-pentylcyclohexanecarboxylate.

Example I

A mixture is prepared from
19% of 2β-cyano-2α-heptyl-6β-propyl-trans-decalin
18% of 2β-cyano-2α,6β-dipentyl-trans-decalin
11% of p-ethoxyphenyl trans-4-propylcyclohexanecarboxylate
9% of 4-(trans-4-pentylcyclohexyl)-4'-(trans-4-propylcyclohexyl)-biphenyl
28% of 4-ethyl-2'-fluoro-4'-(trans-4-pentylcyclohexyl)-biphenyl and
15% of trans-1-(p-ethoxyphenyl)-4-propylcyclohexane.

Example J

A mixture is prepared from
18% of 2β-cyano-2α-heptyl-6β-propyl-trans-decalin
17% of 2β-cyano-2α-propyl-6β-pentyl-trans-decalin
17% of 2β-cyano-2α,6β-dipentyl-trans-decalin
10% of 2β-cyano-2α-propyl-6β-heptyl-trans-decalin
24% of 4-butyl-2-cyanophenyl p-(trans-4-propylcyclohexyl)benzoate and
14% of trans-1-(p-ethoxyphenyl)-4-propylcyclohexane.

Example K

A mixture is prepared from
19% of 2β-cyano-2α-pentyl-6β-propyl-trans-decalin
31% of 2β-cyano-2α-propyl-6β-pentyl-trans-decalin
33% of 2β-cyano-2α,6β-dipentyl-trans-decalin and
17% of 4-(trans-4-pentylcyclohexyl)-4'-(trans-4-propylcyclohexyl)-biphenyl.

Example L

A mixture is prepared from
11% is 2β-cyano-2α-pentyl-6β-propyl-trans-decalin
25% of 2β-cyano-2α-heptyl-6β-propyl-trans-decalin
21% of 2β-cyano-2α-propyl-6β-pentyl-trans-decalin
22% of 2β-cyano-2α,6β-dipentyl-trans-decalin
13% of 2β-cyano-2α-propyl-6β-heptyl-trans-decalin and
8% of trans-4-propylcyclohexyl p-(trans-4-propylcyclohexyl)-benzoate.

Example M

A mixture is prepared from
22% of 2β-cyano-2α-heptyl-6β-propyl-trans-decalin
20% of 2β-cyano-2α,6β-dipentyl-trans-decalin
18% of trans-4-propylcyclohexyl trans-4-pentylcyclohexanecarboxylate
10% of 4-(trans-4-pentylcyclohexyl)-4'-(trans-4-propylcyclohexyl)-biphenyl and
30% of 4-ethyl-2'-fluoro-4'-(trans-4-pentylcyclohexyl)-biphenyl.

Example N

A mixture is prepared from
17% of 2β-cyano-2α,6β-diphenyl-trans-decalin
43% of trans-4-propylcyclohexyl trans-4-propylcyclohexanecarboxylate
16% of trans-4-propylcyclohexyl trans-4-pentylcyclohexanecarboxylate and
17% of 4-butyl-2-cyanophenyl p-(trans-4-propylcyclohexyl)-benzoate.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A decalin-carbonitrile of the formula

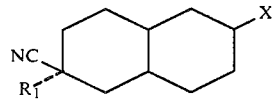

wherein $R^1$ is α—$C_{1-10}$—alkyl, and the 2—CN group is in the β-configuration;

X is a radical selected from the group consisting of alkyl, alkoxy, 4-alkylcyclohexyl, 5-alkyl-1, 3-dioxanyl, 4-alkyl-cyclohexane-carbonyloxy, 2-alkyl-pyrimidine-5-carbonyloxy, p-$R^2$-phenyl carbonyloxy, p-$R^2$-phenyl, and p-$R^2$-phenoxymethyl;

$R^2$ is alkyl, alkyl with one or two non-adjacent $CH_2$ groups replaced by O atoms, F, Cl, Br, CN, —O—$COR^3$, —$COOR^3$, or H and $R^3$ is alkyl of 1 to 6 C atoms;

or an acid addition salt of said compounds which are basic.

2. A compound of claim 1 wherein X is alkyl or alkoxy.

3. A compound of claim 1 wherein X is 4-alkylcyclohexyl is Cy.

4. A compound of claim 1 wherein the total number of C- and oxa-atoms in $R^1$ and $R^2$ is 2–7.

5. A compound of claim 1 wherein X is alkyl.

6. A compound of claim 1 wherein the decalin group is in the trans-configuration, the $R^1$ and X groups are equatorial and the CN group is axial.

7. A liquid crystal dielectric useful for electrooptical display elements comprising at least two liquid crystal components, wherein at least one component is a compound of claim 1.

8. In an electrooptical display element comprising a liquid crystalline dielectric, the improvement wherein the dielectric is that of claim 7.

9. A compound of claim 1, wherein X is alkyl, alkoxy, 4-alkylcyclohexyl, 5-alkyl-1,3-dioxanyl, 4-alkyl-cyclohexanecarboxylate, 2-alkyl-pyrimidine-5-carboxylate p-fluoro or p-cyanophenyl carboxylate; phenyl; or p-alkylphenoxymethyl.

10. A compound of claim 9, wherein the cyclohexane rings are trans configured.

11. A compound of claim 1, wherein X is trans-4-alkylcyclohexyl or 4-$R^2$-phenyl.

12. A compound of claim 11, wherein $R^2$ is alkyl, alkyl with one or two non-adjacent $CH_2$ groups replaced by O atoms, F, Cl, Br or CN.

* * * * *